US005773653A

United States Patent [19]

Baniel

[11] Patent Number: 5,773,653
[45] Date of Patent: Jun. 30, 1998

[54] RECOVERY OF CARBOXYLIC ACID FROM ORGANIC SOLUTION THAT CONTAINS AN AMINE AND AND AN EXTRACTION ENHANCER

[75] Inventor: Avraham Matitiyahu Baniel, Jerusalem, Israel

[73] Assignee: Innova S.A., Luxembourg

[21] Appl. No.: 750,089

[22] PCT Filed: Jun. 21, 1995

[86] PCT No.: PCT/EP95/02399

§ 371 Date: Dec. 6, 1996

§ 102(e) Date: Dec. 6, 1996

[87] PCT Pub. No.: WO96/01247

PCT Pub. Date: Jan. 18, 1996

[30] Foreign Application Priority Data

Jul. 4, 1994 [IL] Israel ......................................... 110206

[51] Int. Cl.⁶ .................................................. C07C 51/42
[52] U.S. Cl. .......................................................... 562/580
[58] Field of Search ............................ 562/580; 435/139, 435/140

[56] References Cited

U.S. PATENT DOCUMENTS

| | | |
|---|---|---|
| 2,581,452 | 8/1952 | Solomon. |
| 4,275,234 | 6/1981 | Baniel et al. ............................ 562/580 |
| 5,426,219 | 6/1995 | Baniel .................................... 562/584 |

FOREIGN PATENT DOCUMENTS 379583  1/1986  Austria.

*Primary Examiner*—C. Warren Ivy
*Assistant Examiner*—Jean F. Vollano
*Attorney, Agent, or Firm*—Browdy and Neimark

[57] ABSTRACT

Recovery of carboxylic acid from an amine-based, water-immiscible organic extractant solution thereof that contains an extraction enhancer, by extraction of acid into an aqueous phase. In a preliminary step the enhancer is removed from the extractant solution by extraction with an aqueous solution containing at least 50 % by weight of a salt of the carboxylic acid present in the extractant. The process is applicable to the recovery of carboxylic acid from a fermentation broth.

15 Claims, 3 Drawing Sheets

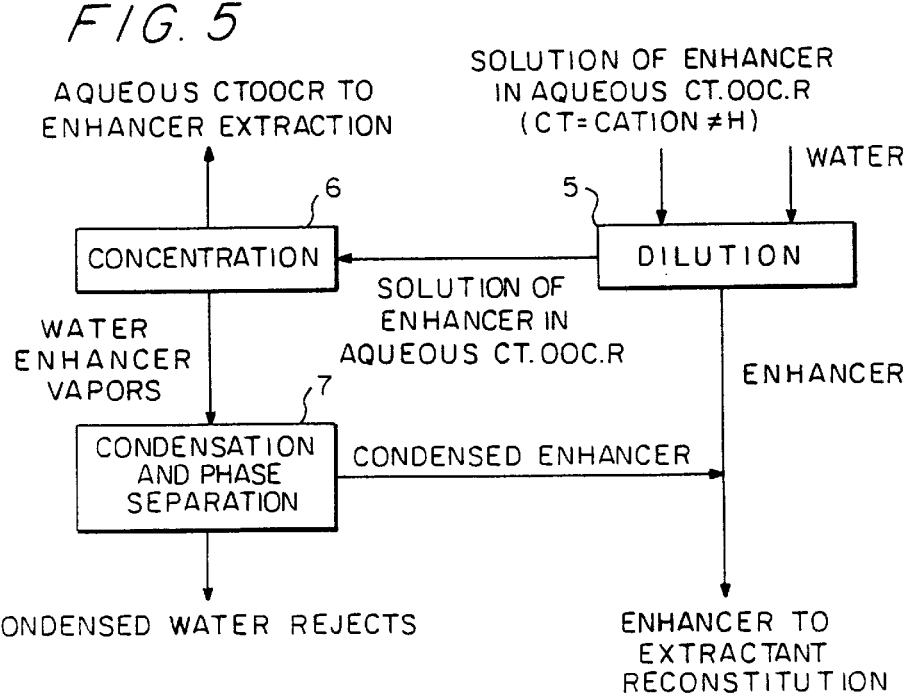
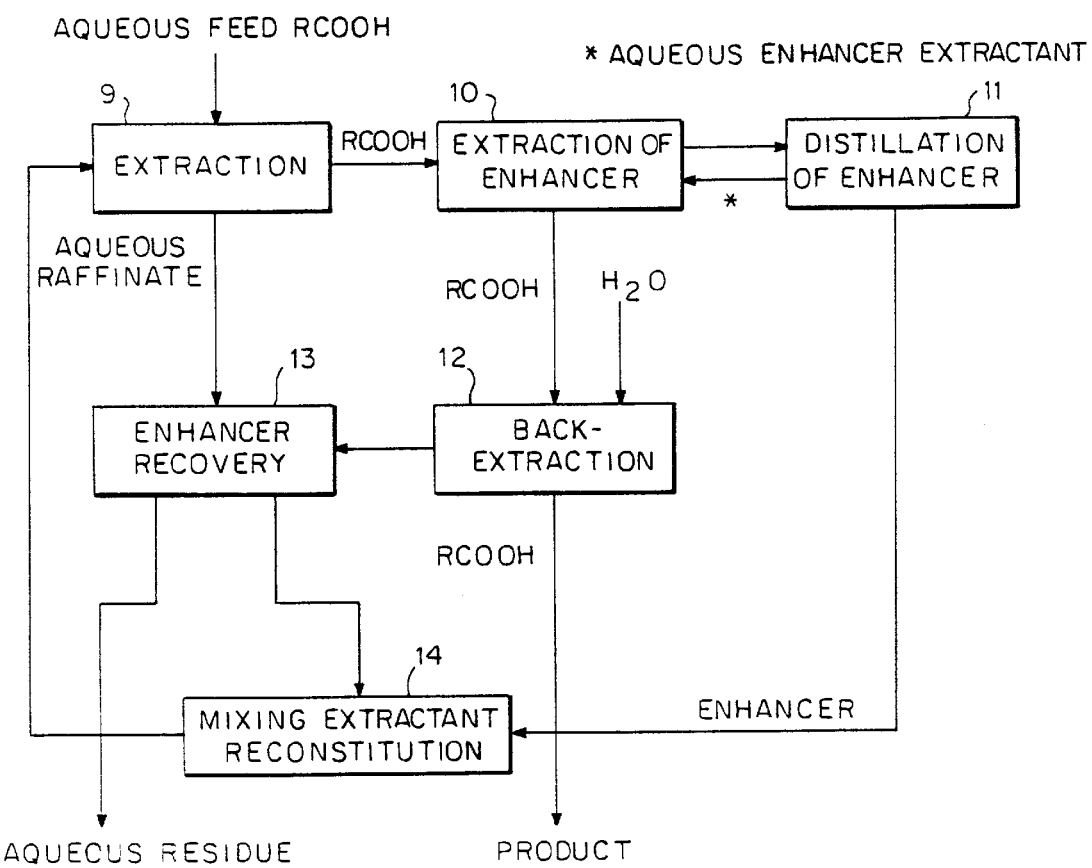

RECOVERY OF CARBOXYLIC ACID FROM ORGANIC SOLUTION THAT CONTAINS AN AMINE AND AND AN EXTRACTION ENHANCER

FIELD OF THE INVENTION

The present invention concerns quite generally the recovery of a carboxylic acid from an amine-based, water-immiscible organic extractant solution thereof obtained by liquid-liquid contact extraction of carboxylic acid from an aqueous starting solution. The amine-based extractant used for the extraction of the starting solution contains (i) a primary, secondary or tertiary long-chain alkyl amine in which the aggregate number of carbon atoms is at least 20; (ii) a liquid hydrocarbon; and (iii) a polar, non-carboxylic organic compound which during the extraction of the carboxylic acid from the aqueous starting solution serves as extraction enhancer. One typical, but not exclusive, field of application of the invention is the recovery of a carboxylic acid from an aqueous fermentation broth, comprising in a first stage a liquid-liquid contact extraction of the fermentation broth with an extractant of the kind specified and in a second stage back-extraction of the carboxylic acid from the organic extractant solution into an aqueous phase.

BACKGROUND OF THE INVENTION

The extraction of carboxylic acid from aqueous solutions by amine-based, water-insoluble organic extractants was described for the first time by Smith and Page, J. Soc. Chem. Ind, 67.48 (1948). Since then, numerous studies were published and a number of industrial processes established. Typical of the latter is the recovery of citric acid from fermentation broths described in U.S. Pat. No. 4,275,234 (Baniel, et al.), according to which the acid is extracted at low temperature with an amine-containing, water-immiscible organic extractant and subsequently recovered as an aqueous solution by back-extraction with water at a higher temperature. As described in U.S. Pat. No. 4,275,234 and as indeed has become common practice, the extraction power of an amine-containing organic extractant is enhanced by the incorporation of a non-carboxylic, neutral polar organic compound, e.g. an alkarol such as n-butanol, a ketone such as butanone, an ester such as butylacetate, an ether such as dibutylether, a bifunctional compound such as $CH_3CH_2CH_2CH_2OCH_2CH_2OH$ etc. Such compounds, generally referred to as enhancers, modifiers or active diluents, increase the base strength of the amine in the extractant and thereby facilitate the transfer of carboxylic acid from the starting aqueous solution such as a fermentation broth, into the organic extractant phase. Put in other words, the presence of an extraction enhancer shifts the carboxylic acid equilibrium in an aqueous phase/organic extractant phase system in favor of the organic phase. This very shifting of equilibrium, however, creates a problem for the back-extraction in that the transfer of the carboxylic acid from the organic-to the aqueous phase is inhibited. In fact, this inhibition may be so pronounced as to render back-extraction of the organic acid with water impractical even at temperatures close to 100° C.

Several approaches have been proposed to overcome this difficulty inherent in carboxylic acid recovery processes of this kind. According to one extreme approach, back-extraction is foregone altogether and carboxylic acid is recovered from the organic extract by distillation. Obviously, this procedure can be considered only for stable, relatively volatile acids such as acetic acid.

By another approach, back-extraction is carried out above the water boiling temperature so as to increase the degree of hydrolysis of the amine-carboxyl complex and thereby provide for an acceptable rate of back-extraction. This approach requires operation at above atmospheric pressure which is inconvenient and costly in terms of equipment and process control.

By yet another approach the enhancer is removed from the organic phase by distillation prior to back-extraction as described in an extensive study "Extraction of Carboxylic Acids with Amine Extractants", Ind. Eng. Chem. Res. 1990, 29, 1319–1338 in the context of what is described there as "diluent swing". This approach requires that the extractant be so composed that the enhancer boils well below all other constituents and that no decomposition of amine, carboxylic acid or enhancer takes place at the distillation temperature. Even where these requirements can be met, costly, energy-consuming vacuum distillation is as a rule required.

To sum up, the two-stage recovery of carboxylic acid from an aqueous starting solution involving extraction of the starting solution with an organic amine-based extractant and then back-extraction of the carboxylic acid from the organic extractant into an aqueous phase, poses a technical dilemma with regard to the use of extraction enhancers: while on the one hand the use of an extraction enhancer is highly desirable in the first stage for the purpose of increasing the extraction yield, it impedes the performance of the second stage. There has thus been a long-felt need to solve the problem and provide a method by which carboxylic acid can be effectively recovered from an organic, water-immiscible amine-based extractant solution that also contains an extraction enhancer of the kind specified. It is the object of the present invention to provide such a method.

BRIEF DESCRIPTION OF THE INVENTION

The invention makes use of an effect by which salts in aqueous solution may act as solubilizer and which, broadly speaking, is a reversal of the salting out effect. Salting out, which is a well known and widely applied effect, means that where a salt of good water solubility is dissolved in an aqueous solution holding a less soluble solute, the latter will precipitate increasingly with the increase of the amount of dissolved salt. In certain cases, where the concentration of the added salt exceeds a critical value at which the salting out is at its highest and the amount of solute remaining in solution at its lowest, a further increase of the concentration of the added salt has been observed to cause solubilization of the solute with the result that a stable solution forms from which the solute is not readily separable. Such a solubilization effect does occur only in some cases and it is unpredictable when it will occur and when not.

The salting out effect can be demonstrated by the precipitation of an n-propanol and n-butanol from their aqueous solutions upon the addition of NaCl, as demonstrated in the following Table 1 in which the data are copied from R. DeSantis et al., The Chem. Eng. J., 1976 pp. 207–214:

TABLE 1

| NaCl, wt % | 0 | 10 | 15 | 20 | 25.5* |
|---|---|---|---|---|---|
| Solubility of nPrOH | infinite | 17 | 9 | 6 | 3 |
| Solubility of nBuOH | 8 | 3.2 | 2.2 | 1.4 | 0.8 |

*Saturation value

It follows from the above Table 1 and from data in many other publications, that the solubility of alkanols and other neutral organic compounds in water is consistently decreased with the increase of the amount of an added inorganic salt, all the way up to saturation of that salt.

With salts of carboxylic acids, however, the situation can be very different. Thus, when NaCl is replaced by sodium lactate one notes a similar salting-out effect up to about 40% salt concentration, but as the lactate concentration increases further beyond that critical point, the solubilities of n-propanol and n-butanol invert and they actually increase after going through minima, as shown in the following Table 2:

TABLE 2

| Na-Lactate, wt % | 0 | 10 | 20 | 30 | 40 | 50 | 60 |
|---|---|---|---|---|---|---|---|
| Solubility of nPrOH | infinite | high | 19 | 12 | 9 | 11 | 21 |
| Solubility of nBuOH | 8 | 4 | 3 | 2 | 1.5 | 2 | 3 |

The above effect is even more pronounced with K-lactate as shown in the following Table 3:

TABLE 3

| K-Lactate, wt % | 0 | 10 | 20 | 30 | 40 | 50 | 60 |
|---|---|---|---|---|---|---|---|
| Solubility of nPrOH | infinite | high | 23 | 21 | 13 | 19 | >40 |
| Solubility of nBuOH | 8 | 4 | 3 | 2 | 2 | 2 | 5 |

The difference between the solubilization effect of sodium and potassium lactate illustrates a second important feature, namely that the solubilization effect of carboxylic acid salts vary for any given carboxylate with the nature of the cation.

In accordance with the present invention it has now surprisingly been found that a solubilization effect does occur in solutions of carboxylic acids in amine-based extractants which also contain an extraction enhancer. It has further been found that this effect can be adapted for the selective extraction of the enhancer from the organic, water-immiscible amine-based extractant solution of carboxylic acid, by performing the extraction with an aqueous solution of a salt of the carboxylic acid present in the extractant.

In accordance with the invention there is provided in a process of recovering a carboxylic acid from an amine-based, water-immiscible organic extractant solution thereof that contains an extraction enhancer, by extraction of the acid into an aqueous phase, the improvement by which the recovery of the carboxylic acid is preceded by extraction of the enhancer from the extractant solution with an aqueous solution containing at least 50% by weight of a salt of the carboxylic acid present in the extractant solution.

In terms of saturation percentage, the aqueous extractant solution should contain an amount of the said carboxylic acid salt corresponding to at least 50% and preferably at least 80% of the saturation value.

The cation of the carboxylic acid salt dissolved in the aqueous extractant solution can be selected from a large variety of metal and ammonium cations. The salts are best formed in situ by adding to the aqueous extraction solution equivalent amounts of the free carboxylic acid and a base such as, for example, NaOH, KOH, $(CH_3)_4NOH$ and the like. As a rule, lower mono-, di-, tri- and tetraalkyl ammonium salts and lower mono-, di- and trihydroxy- alkyl ammonium salts are preferred since such carboxylic acid salts are better soluble and provide for a higher water solubility of the extractant enhancer. Also, the organic radical such as, for example, the $CH_3$ group in tetramethylammonium, can be expected to contribute to the solubilization of an enhancer with a hydrocarbon moiety such as, for example, butanol. The contribution of alkyl radicals in an ammonium cation to solubilization does, as a rule, increase with the size of the alkyl radicals.

If desired, the ammonium cation of the carboxylic acid salts may also bear hydroxyl groups such as, for example, in the triethanolammonium cation. The hydroxyl groups in such cations contribute to the solubilization of an enhancer that contains a polar moiety able to interact with a hydroxyl group by way of a hydrogen bond, a typical example being a keto group CO in ketonic enhancers such as butanone $CH_3CH_2COCh_3$.

It is to be noted that the most appropriate cation moiety of a carboxylic acid salt to be incorporated in the aqueous solution used for the selective removal of the enhancer from the extractant carboxylic acid solution in accordance with the present invention, as well as process parameters such as temperature, flow rate, residence time etc., can be established in each case by simple experimentation on the basis of the teachings of the present invention.

The invention further provides in a process for the recovery of a carboxylic acid from a fermentation broth which comprises extraction of the fermentation broth with a water-immiscible, amine-based organic extractant that includes an extraction enhancer to yield an extractant solution of carboxylic acid, and recovery of carboxylic acid therefrom by back-extraction into an aqueous phase, the improvement by which recovery of carboxylic acid from the extractant solution is preceded by extraction of the enhancer from the extractant solution with an aqueous solution containing at least 50% by weight of a salt of the carboxylic acid present in the extractant solution; to yield an enhancer-depleted extractant solution of carboxylic acid and an aqueous enhancer solution; the aqueous enhancer solution is separated; and the enhancer is regained from the separated aqueous solution thereof and recycled.

In accordance with one embodiment, the regaining of the extraction enhancer from its aqueous solution is effected by liquid-liquid extraction with recycled, enhancer-free, amine based extractant and the resulting enhancer bearing extractant is recycled.

In accordance with another embodiment, the aqueous enhancer solution is diluted with water whereby extractant separates out as a distinct phase and is recycled.

In accordance with yet another embodiment of the invention applicable to operations in which the boiling point of the enhancer or its azeotrope with water is lower than that of water, the enhancer is regained from the aqueous solution thereof by distillation.

DESCRIPTION OF THE DRAWINGS

For better understanding, the invention will now be described, by way of example only, in the accompanying drawings in which:

FIGS. 4, 5 and 6 are block diagrams of three different embodiments of the invention.

DESCRIPTION OF SPECIFIC EMBODIMENTS

Figure 1:
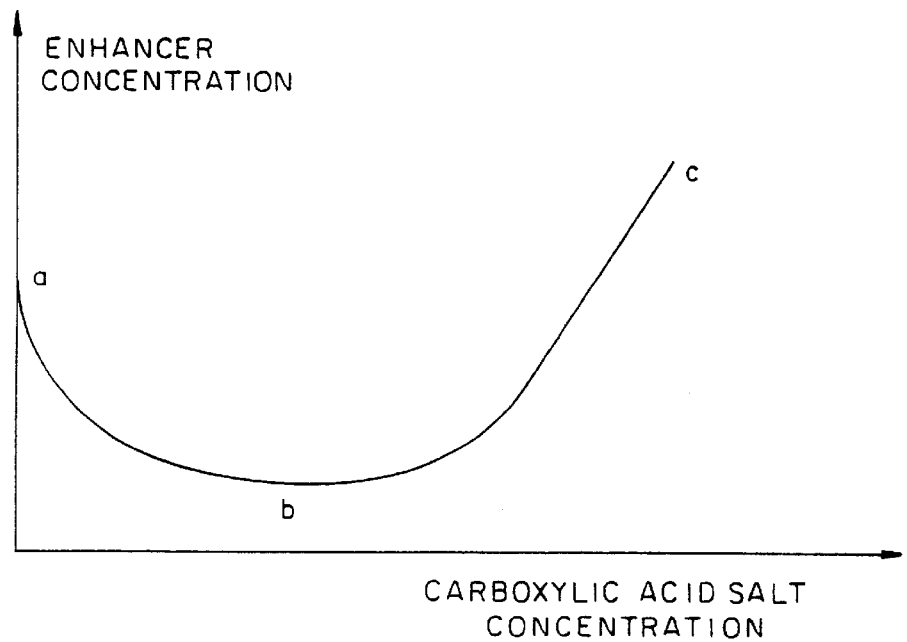
FIG. 1 is a graphical representation illustrating the solubilization of an extraction enhancer by means of a carboxylic acid salt.

FIG. 1 is a graphic representation which plots the solubility of an organic extraction enhancer such as, for example a lower alkanol or ketone, as a function of the concentration of an added carboxylic acid salt. Point (a) on the graph indicates the solubility of the enhancer in pure water, point (b) the amount of dissolved carboxylic acid salt that results in minimum solubility of the enhancer and point (c) the solubility of the enhancer in a saturated aqueous solution of the carboxylic acid salt.

Figure 2:
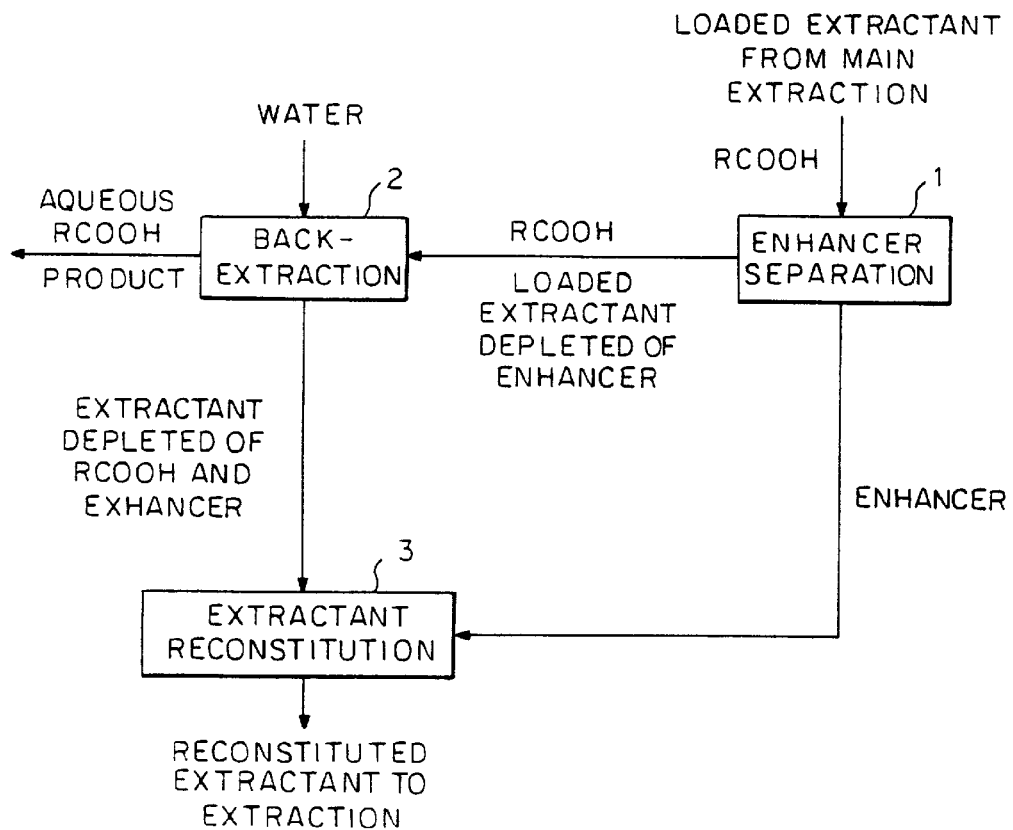
FIG. 2 is a block diagram illustrating in general terms the concept of enhancer separation.

FIG. 2 illustrates in general terms the concept of enhancer separation. As shown, an amine-based extractant which includes an extraction enhancer and is loaded with carboxylic acid, RCOOH is charged into a unit 1 for enhancer separation in accordance with the teachings of the present invention. The extractant emerging from unit 1 is depleted of enhancer but is still fully loaded with carboxylic acid. This enhancer depleted extractant is charged into a unit 2 for back-extraction with water. The resulting aqueous carboxylic acid solution is withdrawn as product while extractant depleted of both carboxylic acid and enhancer is charged into an extractant reconstitution unit 3 where it is mixed with recycled enhancer arriving from the enhancer separation unit 1. The reconstituted extractant is withdrawn from unit 3 and is recycled to extraction of an aqueous starting solution.

Figure 3:
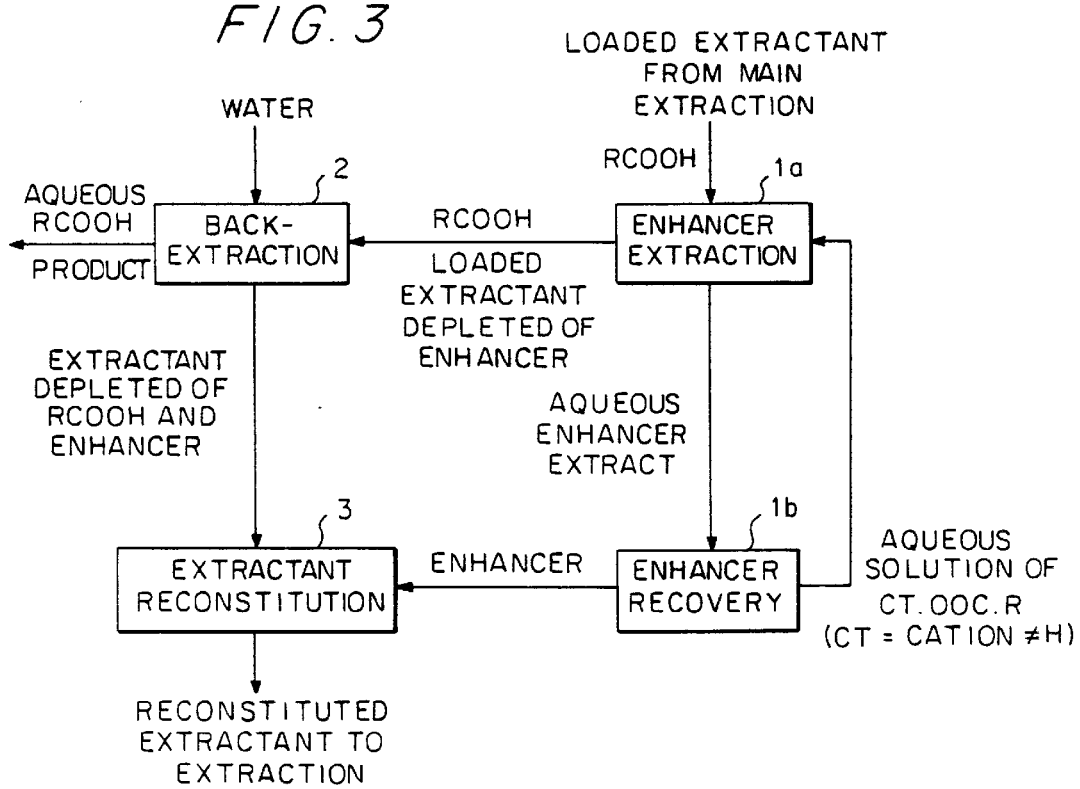
FIG. 3 is a block diagram illustrating in a general fashion the invention.

FIG. 3 illustrates generally the enhancer separation operation in accordance with the invention. As shown, the amine-based extractant which includes an extraction enhancer and is loaded with carboxylic acid, RCOOH is charged into an enhancer extraction unit 1a where it is contacted with an aqueous solution of a salt CtOOCR where Ct is a cation, say a tetraalkyl ammonium salt, of the same carboxylic acid present in extractant unit 1a. Amine-based extractant still loaded with free carboxylic acid and depleted of enhancer is withdrawn from the enhancer extraction unit 1a and charged into unit 2 for back-extraction, similar as in FIG. 2. An aqueous solution containing the said carboxylic acid salt and extracted enhancer is withdrawn from unit 1a and fed into unit 1b where the enhancer is recovered and the remaining aqueous carboxylic salt solution is withdrawn and recycled to unit 1a. The recovered enhancer is fed into the extraction reconstitution unit 3 concurrently withdrawn from back-extraction unit 2 which is depleted of both carboxylic acid and enhancer, and the remainder of the operation is again as in FIG. 2.

Figure 4:
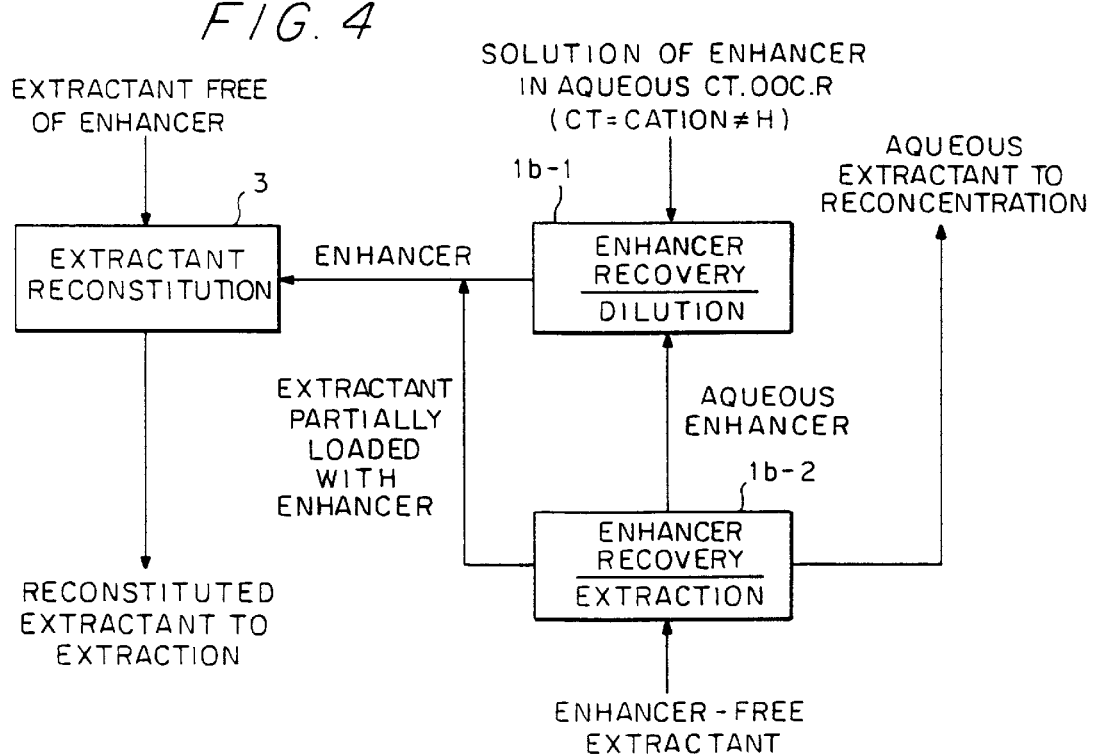

FIG. 4 illustrates one embodiment of the recovery of the enhancer in the performance of the method according to the invention. As shown, the enhancer recovery unit 1b of FIG. 3 is sub-divided into two subunits 1b–1 and 1b–2. The aqueous solution containing carboxylic acid salt CtOOCR where Ct is a cation and enhancer withdrawn from an enhancer extraction unit such as unit 1a in FIG. 3, is charged into the first subunit 1b–1 where it is diluted with water. In consequence, part of the enhancer separates from the aqueous solution with the formation of two liquid phases. The enhancer phase is withdrawn and fed into the extractant reconstitution unit 3. The remaining aqueous enhancer solution which is partially depleted of enhancer, is withdrawn from subunit 1b–1 and charged into subunit 1b–2 where it is contacted with amine-based extractant depleted of both carboxylic acid and enhancer and which is withdrawn from a back-extraction unit such as unit 2 in FIGS. 2 and 3. By this contact the enhancer is extracted from the aqueous solution and the enhancer-loaded extractant is merged with pure extractant withdrawn from subunit 1b–1 and charged into the extractant reconstitution unit 3.

A diluted aqueous solution of carboxylic acid salt is withdrawn from subunit 1b–2 for reconcentration and recycling.

A further embodiment of enhancer recovery is illustrated in FIG. 5. As shown, an aqueous solution containing carboxylic acid salt CtOOCR where Ct is a cation and enhancer withdrawn from an enhancer extraction unit such as unit 1a in FIG. 3, is charged into a dilution unit concurrently with water which leads to the separation of enhancer from the aqueous solution with the formation of two liquid phases. The enhancer phase is withdrawn and sent to extractant reconstitution. An aqueous solution partially depleted of enhancer is withdrawn from unit 5 and charged into a concentration unit 6 from where a reconcentrated aqueous carboxylic acid salt solution on the one hand and water and enhancer vapors on the other hand are separately withdrawn. The vapors are charged into a condensation and phase separation unit 7 from where condensed enhancer is withdrawn and merged with the enhancer arriving from the dilution unit 5, and condensed water is separately withdrawn and rejected.

FIG. 6 shows an overall process for the recovery of carboxylic acid RCOOH from an aqueous fermentation broth, embodying an embodiment of the method according to the invention in which the enhancer is recovered by distillation.

Briefly, the installation includes an extraction unit 9 for the extraction of an aqueous carboxylic acid feed with an amine-based, water-immiscible organic extractant, a unit 10 for the extraction of the enhancer from the acid-loaded extractant in accordance with the teachings of the invention, a unit 11 for the distillation of the enhancer, a back-extraction unit 12, an enhancer recovery unit 13 and an extractant reconstitution unit 14.

In operation crude aqueous carboxylic acid is subjected to liquid-liquid extraction in unit 9 with an amine-based, water-immiscible organic extractant that contains an extraction enhancer, and the resulting acid-loaded extract is fed into unit 10 for the extraction of the enhancer with an aqueous solution of the salt of the carboxylic acid contained in the extractant in accordance with the teachings of the present invention. The enhancer-loaded aqueous solution is conducted into unit 11 where the enhancer is distilled off and the remaining enhancer-depleted aqueous solution is returned to the extraction unit 10 for extraction of the enhancer.

Extractant loaded with carboxylic acid and depleted of enhancer is charged into the back-extraction unit 12 concurrently with water, and the resulting aqueous carboxylic acid solution is withdrawn as product.

An aqueous raffinate which holds some dissolved enhancer is withdrawn from the extraction unit 9 and charged into the enhancer recovery unit 13 together with amine-based extractant withdrawn from the back-extraction unit 12. In consequence of the contact between the two phases, the enhancer is re-extracted into the extractant and the so partly reconstituted extractant is charged into reconstitution unit 14 where it is mixed with further amounts of extractant withdrawn from the distillation unit 11, and the so-reconstituted extractant is recycled into the extraction unit 9.

An aqueous residue is withdrawn as waste from this enhancer recovery unit 13.

The foregoing specific disclosure clearly teaches the salient features of the method of the present invention and on the basis thereof a person skilled in the art can readily select reactants and process parameters for his specific needs with the aid of only some rudimentary experiments.

The present invention enables effective use of low molecular weight, highly water-soluble and volatile enhancers such as ethanol and acetone, which in certain cases may provide for a further advantage. Thus, for example, ethanol at 3% concentration in a given amine-based extractant is approximately equivalent to 10% of octanol in the same extractant. However, if the carboxylic acid needs to be recovered from a dilute aqueous solution such as a fermentation broth, an enhancer such as ethanol will report significantly to the aqueous extraction residue raffinate, thereby imposing an onerous enhance recovery operation by distillation of the raffinate, in addition to the enhancer separation from the organic carboxylic acid extract. In the scheme shown in FIG. 6 a volatile enhancer is partly recovered only from the concentrated aqueous solution of carboxylic acid salt solution withdrawn from unit 10 by distillation, which is much more effective than recovery of the same volatile enhancer from a large volume of extractant loaded with carboxylic acid, and the rest of the enhancer that had separated to the raffinate is regained therefrom by extraction in the manner shown in FIG. 6.

I claim:

1. In a process of recovering a carboxylic acid (1) from an amine-based, water-immiscible organic extractant solution (2) thereof that contains an extraction enhancer, by extraction of the carboxylic acid (1) into an aqueous phase, the improvement wherein the recovery of the carboxylic acid (1) is preceded by extraction of the extraction enhancer from the organic extractant solution (2) with an aqueous solution (3) containing at least 50% by weight of a salt of said carboxylic acid (1) present in said extractant solution.

2. The method of claim 1, wherein the amount of carboxylic acid salt in the aqueous solution corresponds to at least 50% of the saturation value.

3. The method of claim 1, wherein the amount of carboxylic acid salt in the aqueous solution corresponds to at least 80% of the saturation value.

4. The method of claim 1, wherein said carboxylic acid salt is a member of the group of mono-, di-, and tetraalkyl ammonium salts.

5. The method of claim 1, wherein said carboxylic acid salt is a trihydroxyalkyl ammonium salt.

6. In a process for the recovery of a carboxylic acid (1) from a fermentation broth which comprises extraction of the fermentation broth with a water-immiscible, amine-based organic extractant that includes an extraction enhancer to yield an organic extractant solution (2) of carboxylic acid (1), and recovery of said carboxylic acid (1) therefrom by back-extraction into an aqueous phase (3), leaving behind an acid depleted fermentation broth, the improvement wherein recovery of said carboxylic acid (1) from said organic extractant solution (2) is preceded by extraction of the extraction enhancer from the organic extractant solution (2) with an aqueous solution containing at least 50% by weight of a salt of the carboxylic acid (1) present in the organic extractant solution (2) to yield an extraction enhancer-depleted organic extractant solution (2) of carboxylic acid (1) and a separate enhancer solution (3); and the enhancer is regained from the separate aqueous enhancer solution (3) and recycled leaving behind a residual aqueous phase.

7. The process of claim 6, wherein regaining of the extraction enhancer from said separate aqueous solution is effected by liquid-liquid extraction with recycled enhancer-free, amine-based extractant and the resulting enhancer bearing extractant is recycled.

8. The process of claim 6, wherein said separate aqueous enhancer solution is diluted with water whereby extractant separates out as a distinct phase and is recycled.

9. The process of claim 8, wherein said residual aqueous phase is subjected to extraction with recycled enhancer-free extractant.

10. The process of claim 6, wherein the boiling point of the enhancer is lower than that of water, and the enhancer is regained from said separate aqueous solution thereof by distillation.

11. The process of claim 10, wherein enhancer is recovered from said acid depleted fermentation broth by extraction with recycled extractant free of both carboxylic acid and enhancer.

12. The method of claim 2, wherein said carboxylic acid salt is a mono-, di-, or tetraalkyl ammonium salt.

13. The method of claim 3, wherein said carboxylic acid salt is a mono-, di-, or tetraalkyl ammonium salts.

14. The method of claim 2, wherein said carboxylic acid salt is a trihydroxyalkyl ammonium salt.

15. The method of claim 3, wherein said carboxylic acid salt is a trihydroxyalkyl ammonium salt.

* * * * *